United States Patent [19]

Sensel et al.

[11] 4,000,210
[45] Dec. 28, 1976

[54] SELECTIVE DEHYDROGENATION OF N-PARAFFINS TO N-OLEFINS

[75] Inventors: Eugene E. Sensel, Beacon, N.Y.; Alfred W. King, Phoenix, Ariz.

[73] Assignee: Texaco Inc., New York, N.Y.

[22] Filed: June 23, 1975

[21] Appl. No.: 589,326

[52] U.S. Cl. .................... 260/683.3; 208/DIG. 2
[51] Int. Cl.² .......................................... C07C 5/40
[58] Field of Search ............ 260/683.3; 208/DIG. 2

[56] References Cited

UNITED STATES PATENTS 3,437,587  4/1969  Ellert et al. ............... 208/DIG. 2
3,775,501  11/1973  Kaeding et al. ............ 260/683.3

*Primary Examiner*—Veronica O'Keefe
*Attorney, Agent, or Firm*—T. H. Whaley; C. G. Ries

[57] ABSTRACT n-Paraffins, particularly those having from 5 to 20 carbon atoms, are selectively dehydrogenated to n-olefins by a process employing a catalyst consisting essentially of a noble metal supported on a cation mordenite. Selectivity is achieved by the addition of an organic base, such as quinoline, as catalyst modifier to the n-paraffin stream.

9 Claims, No Drawings

SELECTIVE DEHYDROGENATION OF N-PARAFFINS TO N-OLEFINS

BACKGROUND OF THE INVENTION

This invention relates to an improved process for the preparation of n-olefins by dehydrogenation of n-paraffins. More particularly, it relates to the selective preparation of n-olefins having from 5 to 20 carbon atoms by improvements in the process wherein n-paraffins are dehydrogenated in the presence of a catalyst comprising a noble metal on a cation mordenite base.

Olefins of this type have been prepared by a number of commercial methods including (1) thermal and catalytic cracking of petroleum fractions, (2) thermal cracking of paraffin wax, (3) dehydrochlorination of monochlorinated paraffinic hydrocarbons, (4) polymerization of low molecular weight olefins by the Ziegler process, (5) hydrogenation of fatty acids to alcohols with subsequent dehydration of the alcohol to the olefin, (6) fractionation of natural oils and resins of plants, and (7) catalytic dehydrogenation of saturated hydrocarbons. The instant invention relates to improvements in the last named method.

Straight-chain olefin compounds having from 5 to 20 carbon atoms have a variety of uses. They may be used for the synthesis of other compounds such as aldehydes, alcohols, acids and mercaptans. In addition, they are also valuable in the preparation of synthetic detergents, synthetic rubber and resins and as lubricating oil additives. By catalytic dehydrogenation of n-paraffin compounds, good conversion to olefins can be attained. However, along with the dehydrogenation reaction, a significant amount of isomerization and cyclization occurs, with the result that the product olefin comprises a mixture of various olefinic products, and the selectivity for the desired straight-chain product is often less than 50%. If one wishes to obtain pure n-olefins, it is necessary to separate the various olefin products — a difficult task in view of the closeness in boiling points among the individual olefin hydrocarbons.

It is therefore a prime object of this invention to provide a process for the selective production of n-olefins from n-paraffins where the amount of branched-chain and cyclic by-product is about 15% less. It is another object to obtain such selectivity by improvements in the process of dehydrogenation of n-paraffins in the presence of a mordenite supported noble metal catalyst. Other objects will become apparent from the following description of the invention.

SUMMARY OF THE INVENTION n-Paraffins are selectively dehydrogenated to n-olefins in the presence of a catalyst consisting essentially of a noble metal supported on a cation mordenite in which the cation is preferably sodium. Selectivity is achieved by employing an organic base such as quinoline, as a catalyst modifier. The modifier is either added to the catalyst prior to use or, preferably, is added to the n-paraffin stream.

DETAILED DISCLOSURE

The n-paraffin feedstocks used in the process of this invention are straight-chain hydrocarbons having from 5 to about 20 carbon atoms or mixtures thereof. They are conveniently obtained from hydrocarbon streams in petroleum refining operations. Of particular interest as starting materials are hydrocarbon streams consisting primarily of n-paraffins having from 11 to 14 carbon atoms.

The catalyst consists essentially of a noble metal deposited on a sodium mordenite base. Mordenite is a crystalline aluminosilicate (zeolite) which may be either a natural or synthetic product, the synthetic product being more readily available and more commonly used. Mordenite structures are characterized by parallel sorption channels of uniform cross-section. The sorption channels are parallel to the C-axis of the crystal and are elliptical in cross-section. The sorption channel dimensions of sodium mordenite, based on crystallographic studies, have been reported as having a minor diameter of 5.8 to 5.9 A., a major diameter of 7.0 to 7.1 A. and a free diameter of 6.6 A.; the hydrogen form of mordenite is believed to have somewhat larger pore openings with a minor diameter of not less than about 5.8 A. and a major diameter less than 8 A. Structurally, mordenite is significantly different from other zeolites. Mordenite has a chain-type zeolite structure in which a number of chains are linked together into a structural pattern with parallel sorption channels similar to a bundle of parallel tubes. In contrast thereto, type X and type Y synthetic zeolites and faujasite have three-dimensional crystalline cage structures having four to six windows or pore openings per unit cell through which access may be had to the inner cavity or unit cell of the zeolitic molecular sieve. The three-dimensional molecular sieve structure characteristic of most zeolites contributes to catalytic activity in a number of hydrocarbon conversion reactions. However, for the selective dehydrogenation of n-paraffins to olefins, the mordenite structure is markedly superior.

Synthetic mordenites are commercially available from the Norton Company under the trademark Zeolon. These mordenites have a chemical composition, on a unit cell basis, of

$$M_{8/n} \cdot Al_8 \cdot Si_{40} \cdot O_{96} \cdot 24H_2O$$

where M may be sodium, hydrogen or some other exchangeable cation, and n is the valence of the cation. The high ratio of silica to alumina of 10:1 in the synthetic mordenite permits complete acid exchange to a stable hydrogen form and imparts excellent chemical and thermal stability. For purposes of this invention, however, the mordenite should be one in which the cations are preferably sodium although a calcium mordenite may also be used. Either of these cations may be replaced in whole or in part by other ions such as magnesium, zinc, lithium, strontium, cadmium, potassium, manganese, barium, cobalt, nickel, copper, or rare earths. A preferable catalyst is sodium mordenite in which no more than about 70% of the sodium ions are replaced by other ions such as magnesium, calcium, lithium, potassium, etc.

The metals deposited on the mordenite include rhodium, ruthenium and the noble metals osmium, iridium, palladium and platinum; particularly platinum. They are deposited by methods well-known in the art such as ion exchange and impregnation techniques. The concentration of noble metal on the mordenite ranges from about 0.2 to about 1.0 weight %.

The catalysts used in this invention can be, and are preferably, matrixed with another refractory material, such as alumina or silica-alumina. Such matrixing improves attrition resistance and regeneration characteristics.

The organic bases which are employed as catalyst modifiers to provide selectivity include amines which are soluble in the n-paraffin stream. These bases have a $K_B$ of from about $10^{-4}$ to about $10^{-10}$ as determined by the equilibrium relationship.

$$K_B = \frac{[RNH_3^+][OH^-]}{[RNH_2]}$$

Included within this definition are pyridines, N-methylanilines, trialkylamines and quinoline. Quinoline is particularly useful in the process of this invention.

The base material is conveniently and preferably added to the n-paraffin stream immediately prior to the dehydrogenation reaction. The amount of base materials employed ranges from about 1 to about 2.0 × $10^{-4}$g/g-catalyst-Hr., preferably from 1.3 to 1.7 × $10^{-4}$g/g-catalyst-Hr.

Rather than employing the organic base material as an additive to the n-paraffin stream, it may be used as a pre-treatment of the catalyst. For example, the mordenite may be soaked with a solution of quinoline in dodecane at room temperature and the dodecane evaporated by heating under vacuum. Other methods of pretreatment known to the art may be used.

The operating conditions employed in the process of this invention are those used in the known dehydrogenation reactions. Broad and preferred ranges are:

|  | Operative | Preferred |
|---|---|---|
| Temperature °F. | 750 — 975 | about 850°F. |
| Pressure, psig | 0 — 50 | about 15 |
| LHSV | 0.25 — 80 | 2—4 |
| H₂/hc mole | 2 — 10 | 3—5 |

The olefin stream resulting from the process of this invention is composed principally (85% or more) of olefin products having the same chain length as the n-paraffin feed. Thus, when the feed is n-dodecane, a typical yield of total olefin product is 14.8%. This product is composed of 0.1% hexene, 0.1% heptene, 0.1% octene, 0.2% decene and 14.2% dodecene, all percentages being based on the paraffin feed.

The invention will be better understood from the following examples, which are included here for illustrative purposes only and are not to be construed as limitations.

EXAMPLE 1 n-Dodecane was dehydrogenated under the following conditions over a 5-hour period:

| Temperature | — 860°F. |
|---|---|
| Pressure | — 15 psig |
| LHSV | — 2.0 |
| H₂/hc mole ratio | — 5.5 | using a catalyst consisting essentially of 0.75% platinum on sodium mordenite.

The catalyst base consisted of Zeolon-Na, a sodium mordenite in 1/8 inch pellets having a surface area of 400 m²/gm., and manufactured by the Norton Company. The catalyst base was dried for 2 hours at 900° F. Sufficient platinum to provide 0.75 wt.% of platinum was obtained in solution of aqueous hexachloroplatinic acid, then diluted with additional water and cooled with wet ice. The cool solution and the catalyst support material were mixed in an evaporating dish and then allowed to stand for one hour with frequent hand-mixing. It was then placed in an oven (225° F.) and stirred occasionally to evaporate the water. When the bulk of the water had evaporated, the temperature was brought to 300° F. and held at that temperature overnight. The platinum deposited catalyst was finally calcined at 900° F. for 2 hours with periodic stirring. The following table shows the results, for a run employing quinoline as an additive to the n-dodecane stream and for a run with no basic additive.

| | Quinoline Vol. % | % Olefin | % Aromatics | % Branched Olefins | Conversion wt.% |
|---|---|---|---|---|---|
| 1 | none | 18.5 | 6.5 | 35.3 | 36.3 |
| 2 | 1.0 | 13.5 | 0 | 1.8 | 15.2 |

Although the conversion rate was lower for Run No. 2 (with quinoline added), the product olefin comprises 98.2% of n-dodecene.

The above-indicated figure for conversion represents the difference between 100 and the percentage of unreacted charge in the product. The calculation is based upon the equation:

$$\% \text{ Conversion} = \frac{\text{Grams Liquid Product}}{\text{Grams Charge}} \times FSL \times FUC \times 100$$

where FSL represents fraction of saturates in liquid and FUC represents fraction of unreacted charge in the saturate fraction.

EXAMPLE 2

The method of Example 1 was repeated using a catalyst consisting essentially of 0.75% platinum on calcium mordenite. The results are shown in the following table:

| Run No. | Quinoline Vol.% | % Olefin | % Aromatics | % Branched olefins | Conversion wt. % |
|---|---|---|---|---|---|
| 3 | none | 15 | 16 | 50.5 | 50.3 |
| 4 | 1.0 | 17 | 4 | 6.9 | 23.3 |

The product olefin comprised 89.1% of n-dodecene. Selectivity is greatly improved, but is not as high as when the catalyst is a sodium mordenite.

EXAMPLE 3

The catalyst used in Run No. 2 of Example 1 was employed for an additional run (Run No. 5) under conditions identical to those of Example 1. No further quinoline was added. The results were as follows:

| % olefin | — 15.5 |
|---|---|
| % aromatics | — 0 |
| % branched olefins | — 2.6 | conversion (wt.%) — 15.8

These data show that there is a residual effect apparently resulting from the presence of quinoline in the catalyst. The product olefin comprised 97.4% of n-dodecene.

What is claimed is:

1. In a process for the preparation of an n-olefin and mixtures of n-olefins having from 5 to 20 carbon atoms by the selective dehydrogenation of an n-paraffin and mixtures of n-paraffins having from 5 to 20 carbon atoms in the presence of hydrogen and a catalyst consisting essentially of a noble metal on mordenite, the improvement which comprises adding to the n-paraffin from about 0.01 wt. % to about 0.02 wt. %, based on the weight of catalyst, of an organic base comprising pyridines, N-methyl anilines, trialkylamines or quinoline having a $K_B$ of from about $10^{-4}$ to about $10^{-10}$.

2. The improvement of claim 1 in which the organic base is quinoline.

3. The improvement of claim 1 in which the mordenite is sodium mordenite.

4. The improvement of claim 1 in which the noble metal is platinum.

5. The improvement of claim 1 in which the n-paraffins have from 11 to 14 carbon atoms and the n-olefins prepared have from 11 to 14 carbon atoms.

6. The improvement of claim 1 in which said n-paraffin is n-dodecane and said n-olefin is n-dodecene.

7. The improvement of claim 1 in which from about 1 to about 2.0 grams of said organic base are added to the n-paraffin stream per gram of said catalyst per hour.

8. The improvement of claim 1 in which said catalyst is pretreated with said organic base.

9. The improvement of claim 1 in which said noble metal is platinum, in which said mordenite is sodium mordenite, and in which said organic base is quinoline.

* * * * *